(12) United States Patent
Klinec et al.

(10) Patent No.: US 9,534,885 B2
(45) Date of Patent: Jan. 3, 2017

(54) APPARATUS FOR DETERMINING A VERTICAL POSITION OF AT LEAST ONE INTERFACE BETWEEN A FIRST COMPONENT AND AT LEAST ONE SECOND COMPONENT AND LABORATORY AUTOMATION SYSTEM

(71) Applicant: Roche Diagnostics Operations, Inc., Indianapolis, IN (US)

(72) Inventors: Darko Klinec, Calw (DE); Michael Koehler, Winnenden (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 32 days.

(21) Appl. No.: 14/175,141

(22) Filed: Feb. 7, 2014

(65) Prior Publication Data

US 2014/0233042 A1 Aug. 21, 2014

(30) Foreign Application Priority Data

Feb. 21, 2013 (EP) .................................... 13156227

(51) Int. Cl.

| | |
|---|---|
| *G01B 11/14* | (2006.01) |
| *G01B 11/02* | (2006.01) |
| *G01N 33/48* | (2006.01) |
| *G01N 21/13* | (2006.01) |
| *G01N 15/04* | (2006.01) |
| *G01N 15/05* | (2006.01) |
| *G01F 23/292* | (2006.01) |

(52) U.S. Cl.
CPC ......... *G01B 11/028* (2013.01); *G01F 23/2921* (2013.01); *G01N 15/042* (2013.01); *G01N 15/05* (2013.01); *G01N 21/13* (2013.01); *G01N 33/48* (2013.01); *G01N 2015/045* (2013.01)

(58) Field of Classification Search
None
See application file for complete search history.

(56) References Cited

U.S. PATENT DOCUMENTS

| | | |
|---|---|---|
| 6,195,158 B1 | 2/2001 | Cadell et al. |
| 6,770,883 B2 | 8/2004 | McNeal et al. |
| 7,227,622 B2 | 6/2007 | Itoh |

(Continued)

FOREIGN PATENT DOCUMENTS

| | | |
|---|---|---|
| EP | 0538031 A2 | 4/1993 |
| JP | S58-019512 A2 | 2/1983 |

(Continued)

*Primary Examiner* — Kara E Geisel
*Assistant Examiner* — Amanda Merlino
(74) *Attorney, Agent, or Firm* — Roche Diagnostics Operations, Inc.

(57) ABSTRACT

An apparatus for determining a vertical position of an interface between a first component and a second component comprising different layers in a sample container comprises a first unit comprising a first emitting light, a first optics, and a first detector; a second unit vertically spaced from the first unit comprising a second emitting light, a second optics, and a second detector; a driving unit to move the first unit and the second unit relative to the sample container; a position sensing unit to output a position sensing signal indicative of a vertical position of the sample container; and a vertical position determining unit to calculate the vertical position of the interface.

14 Claims, 4 Drawing Sheets

(56) References Cited

U.S. PATENT DOCUMENTS

| | | |
|---|---|---|
| 7,473,897 B2 | 1/2009 | Braendle et al. |
| 2005/0205788 A1* | 9/2005 | Itoh ............................... 250/343 |
| 2008/0259316 A1* | 10/2008 | Ehrich et al. ................... 356/71 |
| 2012/0013889 A1 | 1/2012 | Heise |

FOREIGN PATENT DOCUMENTS

| | | |
|---|---|---|
| JP | 4-1567 A | 1/1992 |
| JP | HO5-312804 A | 11/1993 |
| JP | 2000-266760 A | 9/2000 |
| JP | 2004-28962 A | 1/2004 |
| JP | 2006-010453 A | 1/2006 |
| JP | 2011-252804 A | 12/2011 |
| WO | 00/67547 A3 | 11/2000 |
| WO | 2011/001576 A1 | 1/2011 |
| WO | 2011/019576 A1 | 2/2011 |

\* cited by examiner

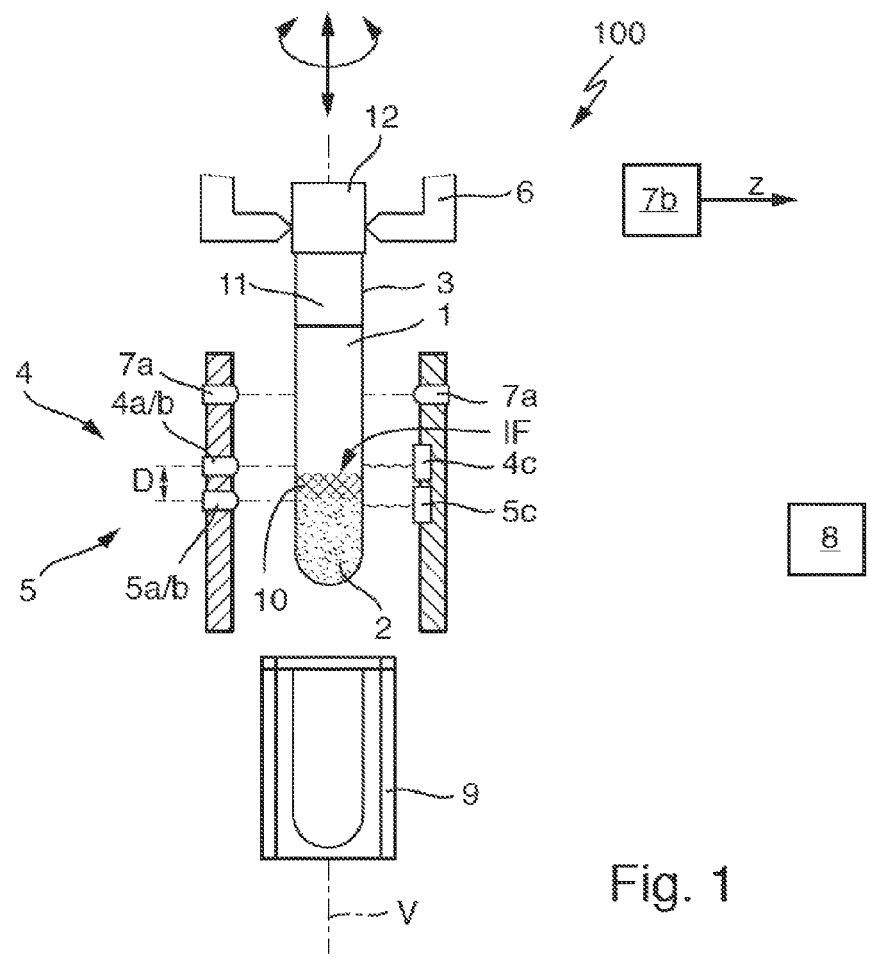
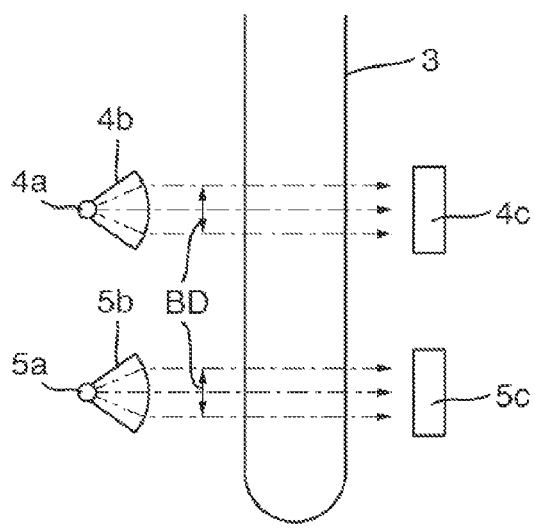
Fig. 1
Fig. 2

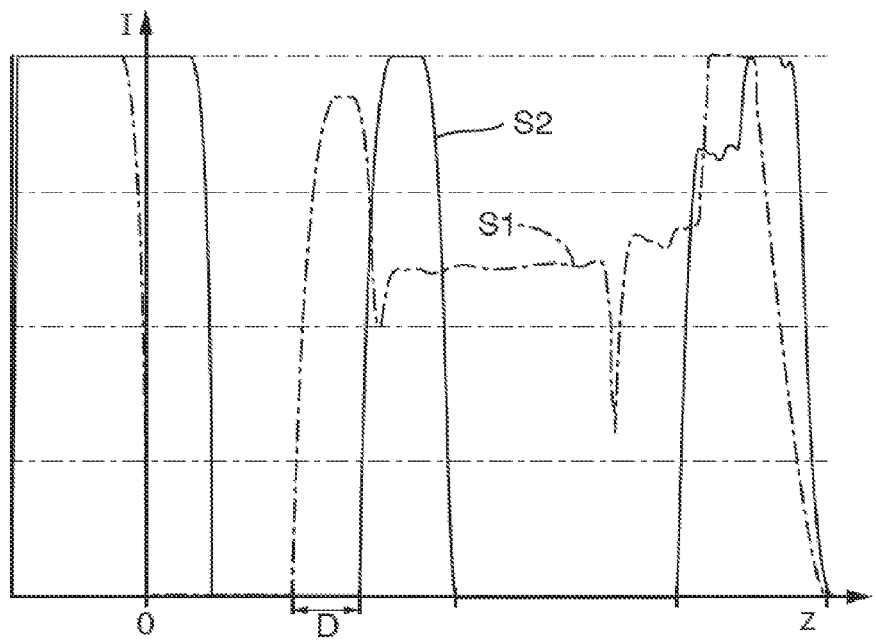
Fig. 3
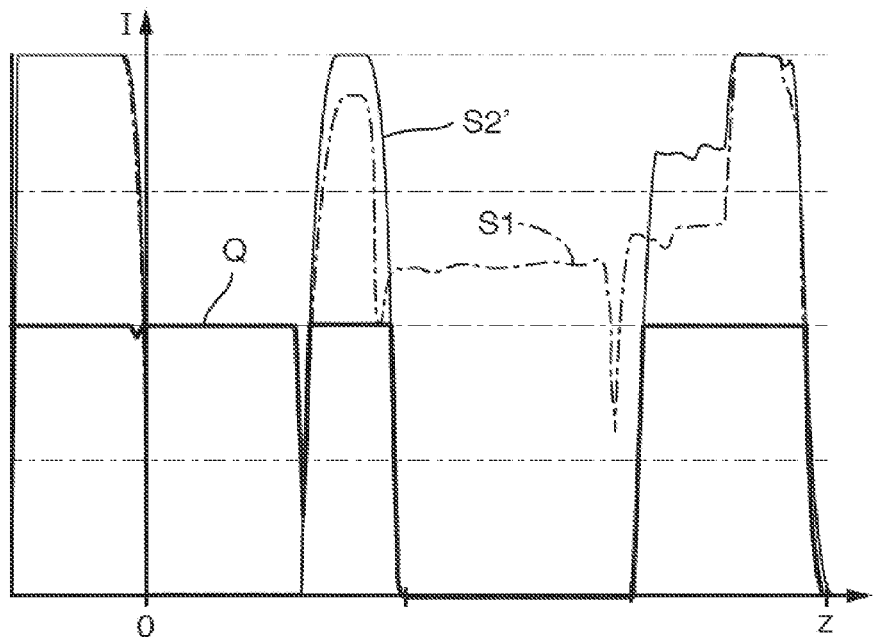
Fig. 4
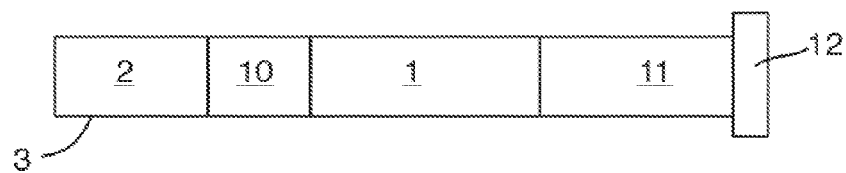

APPARATUS FOR DETERMINING A VERTICAL POSITION OF AT LEAST ONE INTERFACE BETWEEN A FIRST COMPONENT AND AT LEAST ONE SECOND COMPONENT AND LABORATORY AUTOMATION SYSTEM

CROSS-REFERENCE TO RELATED APPLICATIONS

This application is a continuation of EP 13156227.4, filed Feb. 21, 2013, which is hereby incorporated by reference.

BACKGROUND

The present disclosure generally relates to an apparatus for determining a vertical position of at least one interface between a first component and at least one second component, wherein the component comprise different layers in a sample container and to a laboratory automation system.

The prior art discloses an apparatus for determining a vertical position of at least one interface between a first component and at least one second component. The components are comprised as different layers in a sample container or sample tube. This apparatus comprises a first and a second sensing unit at identical vertical positions.

However, there is a need to improve the performance in interface position detection especially when labels are attached to the sample container.

SUMMARY

According to the present disclosure, an apparatus for determining a vertical position of at least one interface between a first component and at least one second component where the components comprise different layers in a sample container is presented. The apparatus can comprise a first sensing unit. The first sensing unit can comprise a first laser diode emitting light having a first wavelength transmitted by the sample container and the first component, a first collimating optics to collimate the light having the first wavelength such that the light can be emitted in form of a beam having a defined diameter and direction in space, and a first light detector generating a first sensing signal in response to an intensity of light having the first wavelength being applied to the first light detector. The apparatus can further comprise a second sensing unit vertically spaced by a given vertical distance from the first sensing unit. The second sensing unit can comprise a second laser diode emitting light having a second wavelength transmitted by the sample container but blocked by the first component, a second collimating optics to collimate the light having the second wavelength such that the light can be emitted in form of a beam having a defined diameter and direction in space, wherein the resulting beam having the second wavelength and the resulting beam having the first wavelength propagate in parallel but vertically spaced paths separated by the given vertical distance, and a second light detector generating a second sensing signal in response to an intensity of light having the second wavelength being applied to the second light detector. The apparatus can also comprise a driving unit to move the sample container relative to the first sensing unit and the second sensing unit, a position sensing unit to output a position sensing signal indicative of a vertical position of the sample container, and a vertical position determining unit to match the first sensing signal and the second sensing signal such that first sensing signal and the second sensing signal can correspond to identical vertical positions and to determine the vertical position of the at least one interface in response to the matched sensing signals and the position sensing signal.

Accordingly, it is a feature of the embodiments of the present disclosure to improve the performance in interface position detection especially when labels are attached to the sample container. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates schematically an apparatus for determining a vertical position of at least one interface between a first component and at least one second component in a sample container according to an embodiment of the present disclosure.

FIG. 2 illustrates schematically light beams generated using collimating optics comprised in the apparatus depicted in FIG. 1 according to an embodiment of the present disclosure.

FIG. 3 illustrates schematically a first and a second sensing signal depending on a vertical position before matching the sensing signals according to an embodiment of the present disclosure.

FIG. 4 illustrates schematically the first and the second sensing signal after matching the sensing signals according to an embodiment of the present disclosure.

DETAILED DESCRIPTION

Figure 5:
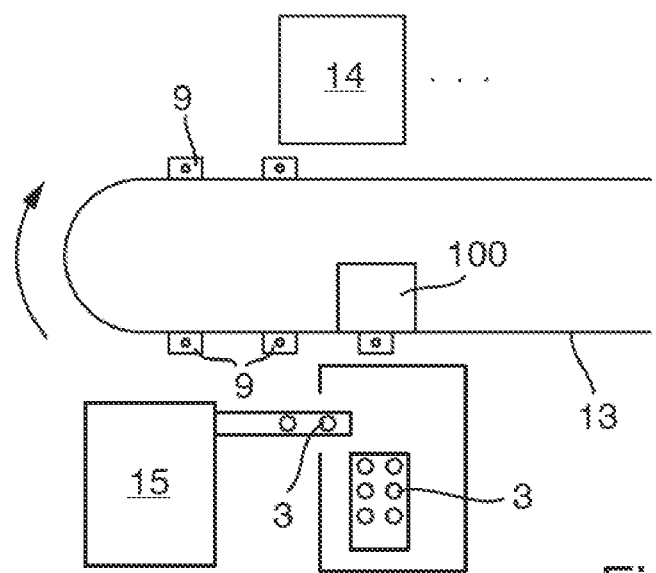
FIG. 5 illustrates schematically a laboratory automation system comprising the apparatus depicted in FIG. 1 according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The apparatus can detect a position of an interface between a first component and a second component. The components can be different layers in a conventional transparent sample container or sample tube as used in automated laboratory instrumentation. For example, the apparatus can detect horizontal interfaces between different layers within a centrifuged sample tube containing blood, such as interfaces between a serum or plasma layer and either a separation medium layer (in sample tubes) or a cruor (blood cell) layer.

The apparatus can comprise a first sensing unit that can include a first laser diode that can emit light having a first wavelength. The first wavelength can be substantially transmitted by the sample container and a first component.

The first sensing unit can further include a first collimating optics to collimate the light of the first wavelength that can be generated by the first laser diode such that the light can be emitted in the form of a beam having a defined diameter and direction in space. The beam may propagate substantially perpendicular to a vertical axis of the sample container, for example, at an angle relative to a vertical axis of the sample container of between about 85 degrees and about 95 degrees such as between about 89 degrees and about 91 degrees. Further, the beam may propagate substantially through the vertical axis of the sample container.

The first sensing unit can further include a first light detector such as, for example, a photodiode or phototransistor, that can generate a first sensing signal, for example a sensing voltage or sensing current, in response to or indicative of an intensity of light having the first wavelength that can reach the first light detector.

The apparatus can further include a second sensing unit vertically spaced by a vertical distance from the first sensing unit. The vertical distance can be specified by design and generally does not change during operation of the apparatus.

The second sensing unit can include a second laser diode that can emit light having a second wavelength. The second wavelength can be substantially transmitted by a sample container but blocked or absorbed by the first component.

The second sensing unit can further include a second collimating optics to collimate the light of the second wavelength generated by the second laser diode such that the light can be emitted in the form of a beam having a defined diameter and direction in space. The beam may propagate substantially perpendicular to a vertical axis of the sample container, for example, at an angle relative to the vertical axis of the sample container of between about 85 degrees and about 95 degrees such as between about 89 degrees and about 91 degrees. Further, the beam may propagate substantially through the vertical axis of the sample container. The resulting beam having the second wavelength and the resulting beam having the first wavelength can propagate in a parallel but vertically spaced path separated by a vertical distance between the first and the second sensing unit.

In some embodiments, the beam generated by the first laser diode and the first collimating optics at the first wavelength and the beam generated by the second laser diode and the second collimating optics at the second wavelength can have substantially identical diameters and substantially parallel propagation directions in space. Beams having substantially identical diameters and directions in space can function to increase the accuracy of interface detection.

The second sensing unit can further comprise a second light detector generating a second sensing signal (such as voltage or current) in response to or indicative of an intensity of light having the second wavelength that can reach the second light detector.

The apparatus can further comprise a driving unit such as, for example, a gripper to grip the sample container, to move the first sensing unit and the second sensing unit relative to the sample container, either together or separately. In some embodiments, the driving unit can provide relative motion between the first and second sensing units and the sample container in both a substantially vertical direction aligned with a central axis of a (cylindrical) sample container or tube and in a rotational direction about the central axis of the (cylindrical) sample container or tube.

The apparatus can further comprise a position sensing unit to output a position sensing signal indicative of a vertical position of the sample container, for example, relative to first sensing unit, or the second sensing unit, or any other given or know relative position. The relative position can, for example, be defined by a light barrier defining a reference vertical position.

The apparatus can further comprise a vertical position determining unit that can match the first sensing signal and the second sensing signal such that first sensing signal and the second sensing signal can correspond to substantially identical vertical positions. The matching can reflect that the first sensing unit and the second sensing unit can be vertically spaced by the given vertical distance such that the first sensor signal and the second sensor signal at a given measurement time can correspond to different vertical positions of the sample container. The matching may be done by a transformation of vertical position coordinates for one of the sensing signals. The vertical position determining unit can further calculate or determine the vertical position of the at least one interface in response to the matched sensing signals and the position sensing signal.

Laser diode light sources can make it possible to detect component interfaces even when labels are attached to the sample container. It is common practice in laboratories that medical and laboratory personnel will add multiple layers of labels (such as 2, 3, 4 or even 5 or more layers) as a sample is processed to yield an analysis result. However, even with the increased intensity provided by laser diode light sources, the detection limit of the disclosed sensing units can be reached or a less than desirable signal to noise ratio can be observed as the number of labels attached to a sample tube increases. Therefore, in some embodiments, the apparatus can further include a mechanism to rotate the relative position of the first and second sensing units about a vertical axis of a sample tube (or at least substantially about its vertical axis) in order to reduce the number of label layers that the light emitted by the laser diodes must pass through before impinging on the light sensors. For example, the sample tube can be rotated or the first and second sensing units can be rotated around the sample tube, or both.

Wavelength specific collimation optics can optimize the detection performance of the apparatus compared to devices having shared collimation optics, that is, beams of multiple wavelengths share an identical measurement path. Shared collimation optics can typically be optimized for one of the wavelengths and thus can have reduced performance for other wavelengths. Alternatively, a compromise can be made such that the collimation optics may not optimal for any of the wavelengths. Finally, by using the matching operation the measurement paths which differ due to the vertical spacing of the sensing units can be virtually matched or aligned with one another, enabling the conventional interface detection for example, on a ratio basis between light beams having different wavelengths.

The vertical position determining unit may further calculate the vertical position of the at least one interface using a ratio between the matched sensing signals. After matching, a quotient between the second sensing signal and the first sensing signal (or vice versa) may be evaluated, wherein the quotient may be compared with a given threshold value. A vertical position for which the result of the comparison changes may be determined as a vertical interface position.

The components may be selected from a group comprising air, (blood) serum or plasma, separation gel, cruor (blood cells) or combinations thereof.

The first wavelength may range between about 400 nm and about 1200 nm and the second wavelength may range between about 1300 nm and about 1700 nm.

As mentioned above, the driving unit may rotate the sample container around a vertical axis of the sample container. As such, the apparatus may repeat the detecting of the vertical position of the at least one interface for the rotated sample container. This can ease the interface detection in case of labels attached to the sample container since by rotating, a measurement path having less label layers may be found enhancing the signal to noise ratio.

The first collimating optics may be specifically adapted to the first wavelength and the second collimating optics may be specifically adapted to the second wavelength, for example, by wave length specific geometric dimensioning, wave length specific materials, and the like.

The driving unit may further insert the sample container into a sample container carrier, into a sample container conveyor, into a sample aliquoter, into an analytical instrument, and the like. The process of interface detection may be simultaneously performed. By performing two tasks, namely interface detection and insertion, in parallel, the overall processing time may be reduced significantly.

A laboratory automation system can process components comprised in a sample container.

Referring initially to FIG. 1, FIG. 1 schematically depicts an apparatus for determining a vertical position of an interface (IF) between a first component in the form of (blood) serum 1 and a second component in the form of a separating medium 10, for example, in the form of a gel. The components 1 and 10 can be comprised as different layers in a sample container or sample tube 3. The sample container 3 can further comprise a third component in form of cruor (blood cells) 2 at the bottom and a fourth component in form of air 11 at the top. The sample tube 3 can be closed by a removable cap 12.

The apparatus can comprise a first sensing unit 4 comprising a first laser diode 4a emitting light having a first wavelength of about 800 nm. Light having this wavelength can be substantially transmitted by the material of the sample container 3 and the serum 1. A corresponding first collimating optics 4b can collimate the light having the first wavelength such that a vertical light beam having a diameter of approximately 0.8 mm can be generated such that the light beam can propagate through the sample tube 3 and the respective component along a vertical measurement path.

A first light detector in the form of a photo diode 4c can be arranged at a vertical level which can be the same as the vertical level of the first laser diode 4a. The photo diode 4c can generate a first sensing signal S1 (see FIGS. 2 and 3) in response to an intensity of light having the first wavelength applied to the photo diode 4c.

The apparatus can comprise a second sensing unit 5 vertically spaced by a given vertical distance D, for example, approximately 10 mm, from the first sensing unit 4. The second sensing unit 5 can comprise a second laser diode 5a emitting light having a second wavelength of about 1550 nm. Light having this wavelength can be substantially transmitted by the material of the sample container 3 but blocked or absorbed by the serum 1. A corresponding second collimating optics 5b can collimate the light having the second wavelength such that a vertical light beam having a diameter of approximately 0.8 mm can be generated propagating through the sample tube 3 and the respective component along a vertical measurement path.

A second light detector in the form of a photo diode 5c can be arranged at a vertical level which can be the same as the vertical level of the second laser diode 5a. The photo diode 5c can generate a second sensing signal S2 (see FIGS. 2 and 3) in response to an intensity of light having the second wavelength being applied to the photo diode 5c.

FIG. 2 schematically illustrates light beams generated using the collimating optics 4b and 5b, respectively. As a result of the collimating optics 5a and 5b, the beam generated by the first laser diode 4a at the first wavelength and the beam generated by the second laser diode 5a at the second wavelength can have substantially identical diameters BD and substantially parallel propagation directions in space. Beams having substantially identical diameters and directions in space can function to increase the accuracy of interface detection compared with embodiments having no collimation optics.

The apparatus can further comprise a driving unit in form of a pick-and-place unit 6 for vertically moving the sample container 3 relative to the first and second sensing unit 4 and 5. The pick-and-place unit 6 can further rotate the sample container 3 around a vertical axis V of the sample container 3.

The apparatus can further comprise a position sensing unit in form of a light barrier 7a and a path sensor 7b. The path sensor 7b can be coupled to the pick-and-place unit 6 and can measure a vertical distance of a movement caused by the pick-and-place unit 6. If the pick-and-place unit 6 vertically moves the sample container 3 from a vertical level above the light barrier 7a towards the light barrier 7a, the light barrier 7a can detect when the sample container 3 disrupts the light path of the light barrier 7a. This vertical position may be defined as a zero or reference position, that is, a position sensing signal z output from the position sensing unit (here path sensor 7b) for this reference position can have a defined reference value such as, for example, zero. Thus, the position sensing unit can output a position sensing signal z indicative of a vertical position of the sample container 3. The vertical position of the light barrier 7a can be defined as a vertical reference position.

A vertical position determining unit 8 such as, for example, a microprocessor, can be coupled to the first and the second sensing unit 4 and 5, the pick-and-place unit 6 and the position sensing unit 7a and 7b.

The vertical position determining unit 8 can control the pick-and-place unit 6 such that the sample container 3 can be sampled along a vertical measurement path. The resulting first sensing signal S1 and the resulting second sensing signal S2 in intensity units as a function of the position sensing signal z are depicted in FIG. 3. To simplify the diagram, the value z=0 of the position sensing signal z can be chosen such that it can correspond to the bottom end of the sample container 3. The first and second sensing signals S1 and S2 can be horizontally misaligned by z=D due to the vertical distance D between the sensing units 4 and 5.

Light having the first wavelength and light having the second wavelength can respectively be blocked or absorbed by the cruor 2 and can respectively be transmitted by the separating medium 10 and air 11. Only the serum 2 can have transmission characteristics depending of the chosen wavelength. Light having the first wavelength can be transmitted by the serum 1 but light having the second wavelength can be blocked or absorbed by the serum 1.

Before analyzing the sensing signals S1 and S2, the vertical position determining unit 8 can match the first sensing signal S1 and the second sensing signal S2. To achieve this, the vertical position determining unit 8 can horizontally shift the sensing signal S2 to the left by z=D, resulting in the matched sensing signal S2', see FIG. 4.

After matching the sensing signals S1 and S2, the vertical position determining unit 8 can compute a quotient Q (including signal smoothing, limiting, and the like) between the matched second sensing signal S2' and the first sensing signal S1. The quotient Q can be compared with a given threshold value. A vertical position for which the result of the comparison changes can be determined as a vertical interface position. As such, the vertical positions of the interfaces between the components (11, 1) and (1, 10) can be computable. The computed vertical interface positions may be used in further processing, for example, when pipetting the sample container 3.

If labels are glued to the sample container 3, the sensing signals S1 and S2 may not have sufficient signal strength. In this case, the driving unit 6 may rotate the sample container 3 around the vertical axis V of the sample container 3 to cause a measurement path eventually crossing a decreased number of label layers and may repeat the measurement. As such, a measurement path having less label layers may be found, thus increasing the signal-to-noise ratio of the sensing signals.

The driving unit 6 can further insert the sample container 3 into a conventional sample container carrier 9. By performing two tasks, namely interface detection and carrier insertion, in parallel, the overall processing time may be reduced.

FIG. 5 schematically illustrates a laboratory automation system comprising the apparatus 100, a centrifuge 15, and an exemplary laboratory station in the form of an aliquoter unit 14. The apparatus 100 and the aliquoter unit 14 can be coupled by a conventional data or field bus. The system may include further laboratory stations, such as pre-analytical stations, analytical stations and post-analytical stations.

The sample containers 3 can be supplied after being centrifuged by the centrifuge 15 or already centrifuged within racks.

The aliquoter unit 14 can transfer part of the serum 1 to one or more secondary tubes (not shown). The aliquoter unit 14 can include a pipetting unit (not shown). The pipetting unit can have a tip (not shown). During aliquoting, the aliquoter unit 14 can control a vertical position of the tip in response to the detected vertical position of the interface IF such that the tip can remain within the serum 1 above the separating medium 10.

The system can further include a sample container transport unit to transport sample containers 3 between the apparatus 100, the aliquoter unit 14 and further laboratory stations (not shown). The sample container transport unit can include a number of sample container carriers 9 and a conveyor 13. The sample container carriers 9 can be attached to the conveyor 13.

Figure 6:
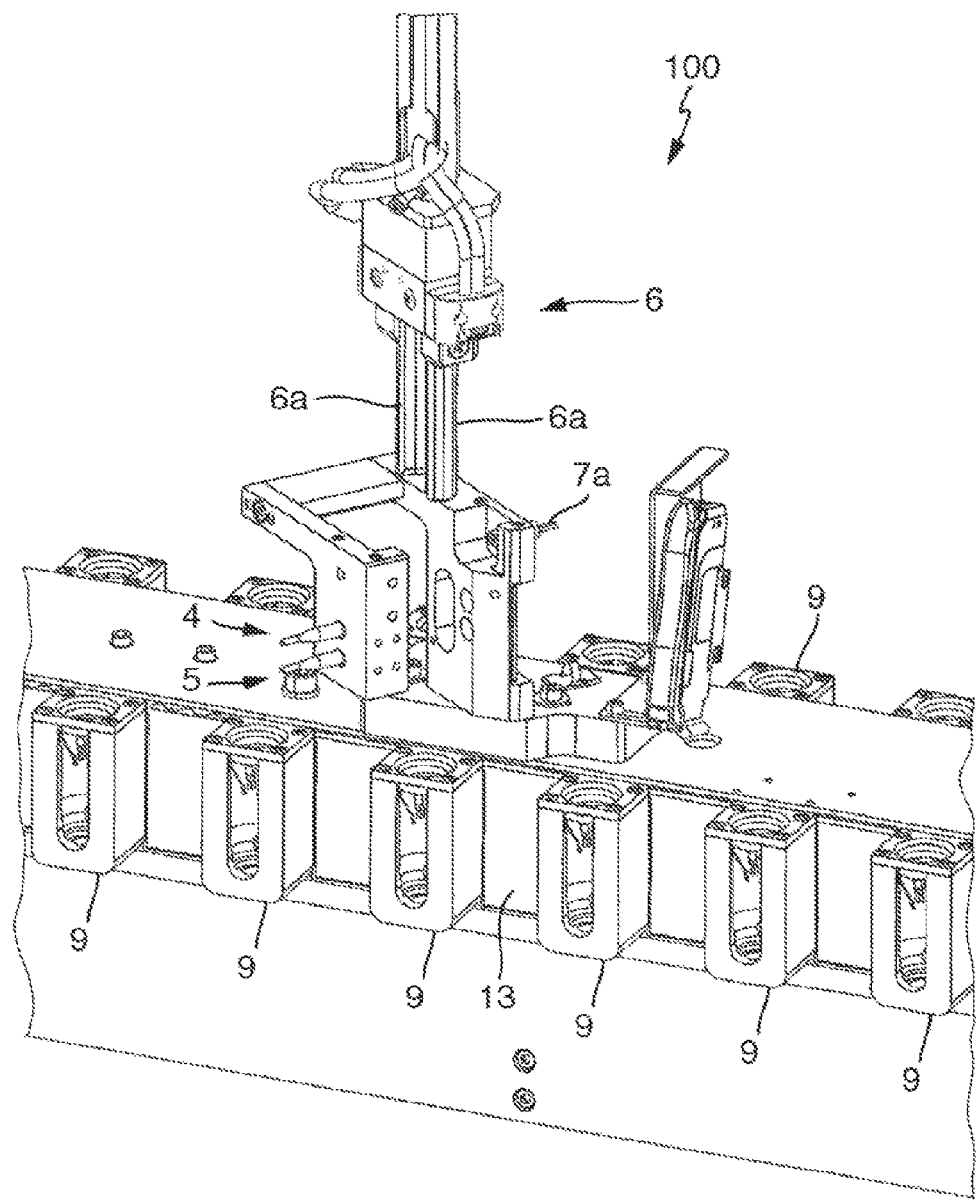
FIG. 6 illustrates schematically aspects of the laboratory automation system depicted in FIG. 5 in more detail according to an embodiment of the present disclosure.

FIG. 6 schematically illustrates the driving unit or pick-and-place unit 6, the first and second sensing unit 4 and 5, the light barrier 7a and the sample container transport unit in more detail.

The driving unit or pick-and-place unit 6 can include a gripper 6a to grip the sample container 3. The driving unit or pick-and-place unit 6 can further provide a relative motion between the first and second sensing units 4 and 5 and the sample container 3 in both a substantially vertical direction aligned with the central axis V of the cylindrical sample container 3 and in a rotational direction about the central axis V of the sample container 3.

The driving unit or pick-and-place unit 6 can insert a sample container 3 into a corresponding sample container carrier 9. The apparatus 100 can simultaneously detect the vertical position of the interface IF. During insertion, the conveyor 13 can be stopped. After insertion, the conveyor 13 can be moved such that an empty sample container carrier 9 can be placed under the pick-and-place unit 6 such that a further sample container 3 may be inserted into the empty sample container carrier 9.

These embodiments can improve the performance in position detection, especially in view of labels attached to the sample container 3 since laser diodes having wave length specific optics can be used. The vertical displacement of the measurement paths can be compensated by virtually matching the different measurement paths.

These embodiments can further improve the overall processing performance since interface detection and insertion of sample in corresponding sample container carriers can be done simultaneously.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An apparatus for determining a vertical position of at least one interface between a first component and at least one second component comprised as different layers in a sample container, the apparatus comprising:
    a first sensing unit comprising,
        a first laser diode emitting light having a first wavelength transmitted by the sample container and the first component,
        a first collimating optics to collimate the light having the first wavelength, such that the light is emitted in form of a beam having a defined diameter and direction in space, wherein the first collimating optics is adapted to the first wavelength, and
        a first light detector generating a first sensing signal in response to an intensity of light having the first wavelength being applied to the first light detector;
    a second sensing unit vertically spaced by a given vertical distance from the first sensing unit comprising,
        a second laser diode emitting light having a second wavelength transmitted by the sample container but blocked by the first component,
        a second collimating optics to collimate the light having the second wavelength such that the light is emitted in form of a beam having a defined diameter and direction in space, wherein the second collimating optics is adapted to the second wavelength, and wherein the resulting beam having the second wavelength and the resulting beam having the first wavelength propagate in parallel but vertically spaced paths separated by the given vertical distance, and a second light detector generating a second sensing signal in response to an intensity of light having the second wavelength being applied to the second light detector;

a driving unit to move the sample container relative to the first sensing unit and the second sensing unit and to simultaneously insert the sample container into a sample container carrier parallel to detecting the vertical position of the at least one interface;

a position sensing unit to output a position sensing signal indicative of a vertical position of the sample container; and a vertical position determining unit to match the first sensing signal and the second sensing signal such that first sensing signal and the second sensing signal correspond to identical vertical positions and to determine the vertical position of the at least one interface in response to the matched sensing signals and the position sensing signal.

2. The apparatus according to claim 1, wherein the vertical position determining unit calculates the vertical position of the at least one interface using a ratio between the matched sensing signals.

3. The apparatus according to claim 1, wherein the first and the second component are selected from a group comprising air, serum, separation gel or combinations thereof.

4. The apparatus according claim 1, wherein the first wavelength ranges between 400 nm and 1200 nm.

5. The apparatus according claim 1, wherein the second wavelength ranges between 1300 nm and 1700 nm.

6. The apparatus according to claim 1, wherein the driving unit rotates the sample container around a vertical axis of the sample container.

7. The apparatus according to claim 6, wherein the apparatus repeats the detecting of the vertical position of the at least one interface for the rotated sample container.

8. The apparatus according to claim 1, further comprising,
a light barrier to detect the introduction of a sample container into the apparatus.

9. The apparatus according to claim 8, wherein the apparatus activates the first and the second sensing unit when the introduction is detected.

10. A laboratory automation system for processing components comprised in a sample container, the system comprising:
the apparatus according to claim 1; and
at least one laboratory station coupled to the apparatus, wherein the at least one laboratory station operates in response to the detected vertical position of the at least one interface.

11. The system according to claim 10, wherein at least one of the laboratory stations is an aliquoter unit having a pipetting unit having a tip, wherein during aliquoting the aliquoter unit controls a vertical position of the tip in response to the detected vertical position of the at least one interface.

12. The system according to claim 10, further comprising,
a sample container transport unit to transport the sample container between different laboratory stations, wherein the sample container transport unit comprises a number of sample container carriers.

13. The system according to claim 12, wherein the sample container transport unit comprises a conveyor.

14. The system according to claim 13, wherein the sample container carriers are attached to the conveyor.

* * * * *